United States Patent [19]

Fine et al.

[11] Patent Number: 4,922,927
[45] Date of Patent: May 8, 1990

[54] TRANSVENOUS DEFIBRILLATING AND PACING LEAD

[75] Inventors: Michael J. Fine, Lake Jackson; Richard V. Calfee, Houston, both of Tex.

[73] Assignee: Intermedics, Inc., Angleton, Tex.

[21] Appl. No.: 348,869

[22] Filed: May 8, 1989

Related U.S. Application Data

[63] Continuation-in-part of Ser. No. 139,839, Dec. 30, 1987, abandoned.

[51] Int. Cl.⁵ ............................................... A61N 1/05
[52] U.S. Cl. ................................... 128/786; 128/419 P
[58] Field of Search ............... 128/786, 419 P, 419 D, 128/789, 785

[56] References Cited

U.S. PATENT DOCUMENTS

| | | | |
|---|---|---|---|
| 4,381,013 | 4/1983 | Dutcher | 128/785 |
| 4,432,377 | 2/1984 | Dickhudt | 128/786 |
| 4,481,953 | 11/1984 | Gold et al. | 128/786 |
| 4,514,589 | 4/1985 | Aldinger et al. | 128/784 |
| 4,640,983 | 2/1987 | Comte | 128/784 |
| 4,677,989 | 7/1987 | Robblee | 128/419 P |

*Primary Examiner*—Lee S. Cohen
*Assistant Examiner*—S. Getzow
*Attorney, Agent, or Firm*—John R. Merkling

[57] ABSTRACT

A transvenous lead for defibrillation and pacing of the heart includes a single defibrillating coil electrode adapted to be introduced into the right ventricle of the heart. The coil constitutes a relatively long flexible large surface area electrode conformable to the shape of the ventricle and thereby readily disposed along the entire length of the vertricle for use in delivering defibrillating shocks. A pacing electrode at the tip of the lead is used both in stimulating the heart with pacing pulses and in sensing the response of the heart to the pulses and to shocks. The coil electrode is multi-filar, composed of a plurality of wires tightly wound side by side, each wire composed of copper-zirconium alloy wrapped with tantalum, and is flared from the diameter at its ends to a lager diameter intermediate its ends to increase the exposed surface area thereof in the ventricle.

29 Claims, 1 Drawing Sheet

TRANSVENOUS DEFIBRILLATING AND PACING LEAD

CROSS-REFERENCE TO RELATED APPLICATION

The present application is a continuation-in-part patent application Ser. No. 139,839 filed Dec. 30, 1987, now abandoned.

BACKGROUND OF THE INVENTION

1. The Field of the Invention

The present invention pertains to transvenous leads for use with implantable cardiac stimulators, and more particularly to a transvenous or catheter lead for use in defibrillating and pacing the heart and in sensing the response of the heart to the defibrillating and pacing stimuli.

2. The Prior Art

Various factors affect the human heart rate and contribute to changes of rate from what is termed the normal sinus rate range. In healthy persons, tachycardia (rates generally ranging in adults from 100 to 160 beats per minutes) is experienced as a result of such things as physical or emotional stress (exercise or excitement), consupmption of alcoholic or caffeinated beverages, cigarette smoking, or ingestion of certain drugs. Rates exceeding 200 pmb have been observed in younger persons during strenuous exercise.

Variation from normal sinus rate range is generally characterized as cardiac arrhythmia, and arrhythmia rates exceeding the upper end of the sinus rate range are termed tachyarrhythmias. Healthy persons usually experience a gradual return to the sinus rate after removal of the factors giving rise to sinus tachycardia.

Arrhythmias typically arise in the atria or ventricles as a consequence of an impairment of the heart's electro-physiologic properties such as excitability, conductivity, and automaticity (rhythmicity). Such arrhythmias require special treatment, and in some instances may require immediate emergency treatment toward preventing sudden death of the afflicted individual. For example, tachycardia may, in certain instances, lead to fibrillation of an affected chamber of the heart. During fibrillation, sections of conductive cardiac tissue of the affected chamber undergo completely uncoordinated random contractions, quickly resulting in a complete loss of synchronous contraction of the overall mass of tissue and a consequent loss of the blood-pumping capability of that chamber.

Because of the lack of contribution of the atrial chambers to cardiac output, atrial fibrillation is hemodynamically tolerated and not generally regarded as life-threatening. However, in the case of ventricular fibrillation, cardiac output ceases instantaneously as a result of the rapid, chaotic electrical and mechanical activity of the excitable myocardial tissue and the consequent ineffectual quivering of the ventricles. Unless cardiac output is restored almost immediately after the onset of ventricular fibrillation, tissue begins to die for lack of oxygenated blood, and death will occur within minutes.

Ventricular fibrillation frequently is triggered by acceleration of a centricular tachycardia. Hence, various methods and devices have been developed or proposed to treat and arrest the tachycardia before the onset of fibrillation. Conventional techniques for terminating tachycardia include pacing therapy and cardioverson. In the latter technique, the heart is shocked with one or more current or voltage pulses of generally considerably higher energy content than is delivered in pacing pulses. Unfortunately, the use of such therapy itself presents a considerable risk of precipitating fibrillation.

Defibrillation involves applying one or more high energy "countershocks" to the heart in an effort to overwhelm the chaotic contractions of individual tissue sections and to re-establish an organized spreading of action potential from cell to cell of the myocardium, thereby restoring the synchronized contraction of the mass of tissue. If these chaotic contractions continue in any tissue section, the defibrillation may be short-lived in that the uncontrolled tissue section remains a potential source for reinitiating fibrillation of the entire mass. Successful defibrillation clearly requires the delivery of a shocking pulse containing a substantial amount of electrical energy to the heart of the afflicted person, at least adequate to terminate the fibrillation and to preclude an immediate re-emergence.

Typically, for transthoracic external defibrillation, paddles are positioned on the patient's thorax and from about 100 to about 400 joules of electrical energy is delivered to the chest area in the region of the heart. By the manner in which the shock is applied, only a portion of this energy is actually delivered to the heart and is available to arrest fibrillation. Where fibrillation occurs during oepn heart surgery, internal paddles may be applied to opposite surfaces of the ventricular myocardium and, in these instances, the energy required to be delivered is considerably less, on the order of 20 to 40 joules.

The pulse energy requirements for internal defibrillation with fully implantable defibrillators and electrode systems range from about 5 joules to approximately 40 joules. Of course, the actual energy level required may differ from patient to patient, and further depends on such factors as the type of pulse waveform and the electrode configuration employed. While advances and improvements in electrical energy sources in general, and pacemaker batteries in particular, have been made over the past few years, it is clear, nonetheless, that repeated delivery of amounts of energy at the higher end of that range from an implanted system will tend to deplete conventional batteries in relatively short order. Accordingly, reduction of the energy level required for internal defibrillation remains a key area of inquiry and investigation.

It is clear that the electrode configuration plays an important role in the amount of energy necessary to achieve successful defibrillation. An early U.S. Patent, in terms of the relative immaturity of developments in the field at the time, U.S. Pat. No. 2,985,172, issued in 1961, described a tissue contacting electrode for use in deliverying a high voltage discharge directly to the heart. Each electrical lead, the ring holding conductive foil members and enclosed in a gauze sock, with a flexible backing member at one side of the sock. The overall electrode pad was described as sufficiently flexible to assume a dished shape tightly engaging the tissue of the heart.

In U.S. Pat. No. 4,030,509, Heilman, et al. describe an implantable electrode system for ventricular defibrillation, in which the electrodes are arranged in a generally base-apex configuration with a split conformal base electrode positioned above the base of the ventricles in the region of the atria, and a cup-like conformal apex electrode positioned at the apex of the heart.

In U.S. Pat. Nos. 4,270,549 and 4,291,707, Heilman, et al. disclose defibrillation electrodes of rectangular shape designed for insertion through the soft tissues outside the pleural cavity for contacting the heart. Each electrode consists of a metallic mesh either sandwiched between two layers of inert electrical insulation material or backed with a single layer of such material stitched to the mesh.

In U.S. Patent No. 4,548,203, Tacker, et al. disclose an electrode system for use with implantable pulse generators employed for cardioversion or defibrillation. The system consists of two sets of opposed patch electrodes, one pair disposed laterally on the epicardium and the other pair disposed ventrally-dorsally, with each electrode orthogonal to the adjacent electrodes. The patent asserts that the presence of the latter pair of electrodes does not significantly alter the current distribution from the first pair, so long as the electrodes are relatively small with respect to the epicardial circumference and the two pairs are isolated from each other during current flow. The patent further ascribes the use of two pairs of electrodes implanted in spaced relationship as purportedly permitting the use of smaller electrodes, lower voltage and current, and lower total energy, with a more uniform current density and less hazard of damage to adjacent heart tissue, than had theretofore been achieved. Two current pulses are sequentially delivered to the separate pairs of electrodes to provide a temporal and spatial summation effect for the defibrillating current.

Nevertheless, such prior art electrode systems proposed for use with implantable defibrillators dissipate relatively large amounts of energy in delivering shocking pulses to the heart. A reduction in the shock strength required for defibrillation provides the advantages of reducing the size of the batteries required and, thus, the size of the implantable defibrillator, increasing battery life, and reducing the possibility of myocardial damage resulting from the shock. In U.S. patent application Ser. No. 019,670, filed Feb. 27, 1987, assigned to the same assignee as the present application, separate large area defibrillation patch electrodes are placed over the right ventricle and the left ventricle of the heart and secured directly to either the epicardium or the pericardium. Each electrode is fabricated from a conductive layer, such as a mesh, with a bio-compatible insulative backing layer overlying one side of the conductive mesh, and an electrically conductive connection between the mesh and a lead for delivering the fibrillating waveform from the implanted (or external) difibrillator to the electrode. Each electrode is contoured to conform to the shape of the heart in the region of the respective ventricle over which it is to be placed, and has a size and shape to encompass a substantial portion of the ventricular myocardium but not other areas of the heart.

Electrodes fabricated according to criteria set forth in the aforementioned commonly assigned application provide a more uniform potential gradient field throughout the entire ventricular mass, lower electrode impedance, and substantially higher efficiencies in the transfer of electrical energy than had theretofore been achieved with prior art defibrillator electrodes. However, as is usual with plural patch electrodes, implantation involves thoracic surgery requiring opening of the patient's chest for epicardial or extrapericardial placement.

It is a principal object of the present invention to provide an improved defibrillator electrode system which is implantable without major thoracic surgery, and which achieves highly efficient transfer of energy.

SUMMARY OF THE INVENTION

Briefly stated, the present invention provides an improved transvenous or catheter lead adapted for introduction into the right side of the heart of a cardiac patient for use in defibrillating and pacing the heart, and in sensing the heart's response to the stimuli. The lead comprises a defibrillating coil formed by at least one continuously wound conductor including an insulated lead portion (coil conductor) and an exposed electrode portion (coil electrode), the latter adapted to be positioned in the right ventricle and configured to present substantial electrode surface area in the ventricle. To that end, the coil electrode is structured to have a length and location along the lead sufficient to extend throughout or virtually throughout the entire length of the ventricular chamber, and may extend into the right atrium, upon placement of the distal tip of the lead at the apex of the ventricle. This coil electrode structure substantially improves the efficiency of delivery of the defibrillating shock stimuli to the heart. The diameter of the mid-section of the coil electrode is materially greater than the diameter of the coil conductor and fully supported by an insulative tubular member, the mid-section being tapered down at either end thereof to the diameter of the conductor. A pacing electrode at the tip of the lead, coupled via its own electrically isolated coil conductor to a stimulus generator, may be used both in stimulating the heart with pacing pulses and in sensing the response of the heart to the pulses and to shocks.

In a preferred embodiment, the defibrillating coil conductor and coil electrode are a continuous multifilar (preferably trifilar) winding composed of a plurality of separately wound adjacent wires. Each wire is composed of copper-zirconium alloy wrapped with tantalum. The coil electrode has a length in the range from six to ten centimeters and is flared to the larger mid-length coil diameter from each end thereof. The exposed surface of the entire coil electrode is coated with a layer of iridium oxide. The defibrillating coil conductor is an extension of the coil electrode, but is insulated from the surrounding tissue and fluid, and electrically couples the coil electrode to a connector to be mated with the connector of an implantable defibrillator.

The pacing electrode is separated from the closest end of the coil electrode by a distance of approximately one centimeter and is electrically insulated therefrom. Preferably, the pacing electrode is also coated with iridium oxide. An active fixation mechanism, such as a conventional corkscrew coupled to the tip of the lead, is used to affix the pacing electrode in proximity to excitable myocardial tissue at the endocardium in the right ventricle.

The multi-filar tantalum-wrapped copper zirconium wire composition provides the defibrillating coil electrode with high tensile strength, breaking weight, hardness and grain size, and low impedance. These properties together with the large exposed surface area attributable to the length and flared configuration of the coil, and the lowered threshold from the iridium oxide coating, render the coil electrode highly efficient in the transfer of energy from the defibrillating electrical shocks to the heart. The shocks are delivered across the coil electrode and either a properly positioned subcutaneous patch electrode or the metal case of the pulse generator. Defibrillation has been achieved at very low energy levels, in the range from 7 to 10 joules, using transvenous leads according to the preferred embodiment of the invention. In the case of the pacing electrode, the iridium oxide coating thereon serves to lower the stimulation threshold and the electrode polarization, for improved stimulation and sensing.

Therefore, another object of the invention is to provide a transvenous lead having an exposed coil electrode for use in delivering defibrillating shocks, and wherein the coil electrode has a configuration and composition which enhances the transfer of electrical energy for defibrillation.

In U.S. Pat. No. 4,662,377, Heilman, et al. disclose an intravascular catheter lead in which distal and proximal spring electrodes, closely wound to about 20 turns per inch, are spaced by from 8 to 14 centimeters along the lead such that when the lead is properly placed, the distal spring electrode is positioned in the right ventricle at the apex and the proximal electrode is positioned in the region of the superior vena cava and right atrium. The proximal electrode is electrically connected to a patch electrode implanted subcutaneously outside the thoracic cavity proximate to the apex of the left ventricle, and a pulse of electrical energy is discharged between the distal electrode and the combined proximal electrode/subcutaneous patch electrode. In contrast to the transvenous lead of the present invention, such a catheter lead employs two separate leads spaced and electrically isolated from one another along the lead, and using separate conductors, and providing relatively small surface area in the ventricle. This prior art lead does not provide the energy efficiency of the coil electrode lead of the present invention, has a relatively complex construction, and is subject to coupling between the distal and proximal electrodes along the catheter lead as well as between the distal electrode and the subcutaneous patch electrode.

Another object of the invention which serves, in conjunction with an electrically isolated subcutaneous patch electrode, to deliver substantially all of the defibrillating shock energy to the ventricular mass in fibrillation.

BRIEF DESCRIPTION OF THE DRAWINGS

The above and still further objects, features and attendant advantages of the present invention will become apparent from a consideration of the following detailed description of a preferred embodiment thereof, taken in conjunction with the accompanying drawings, in which.

DETAILED DESCRIPTION OF THE PREFERRED EMBODIMENT

Figure 1:
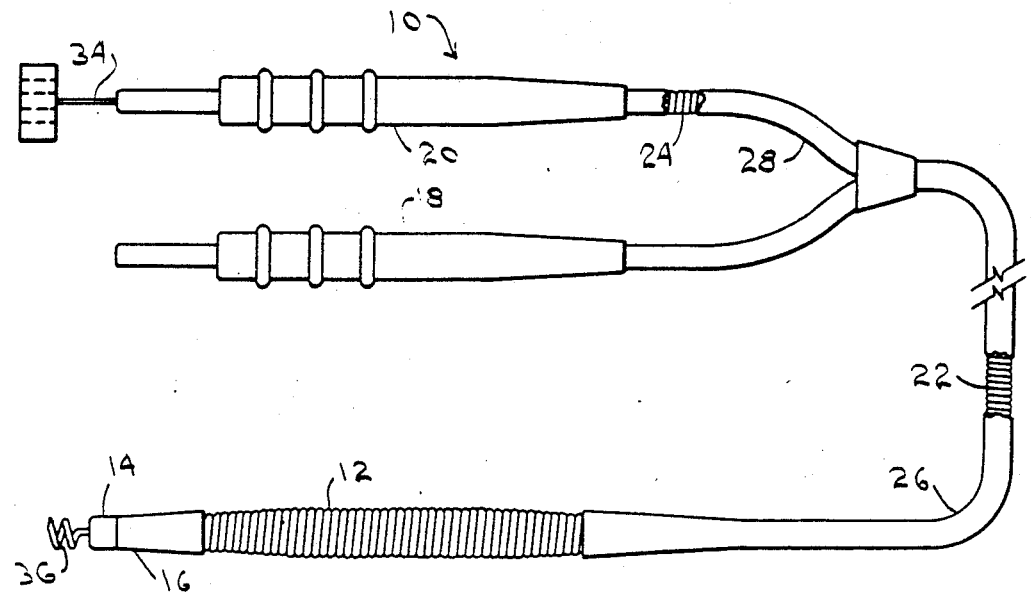
FIG. 1 is a side view of the preferred embodiment of the transvenous defibrillating and pacing lead.
Figure 2:
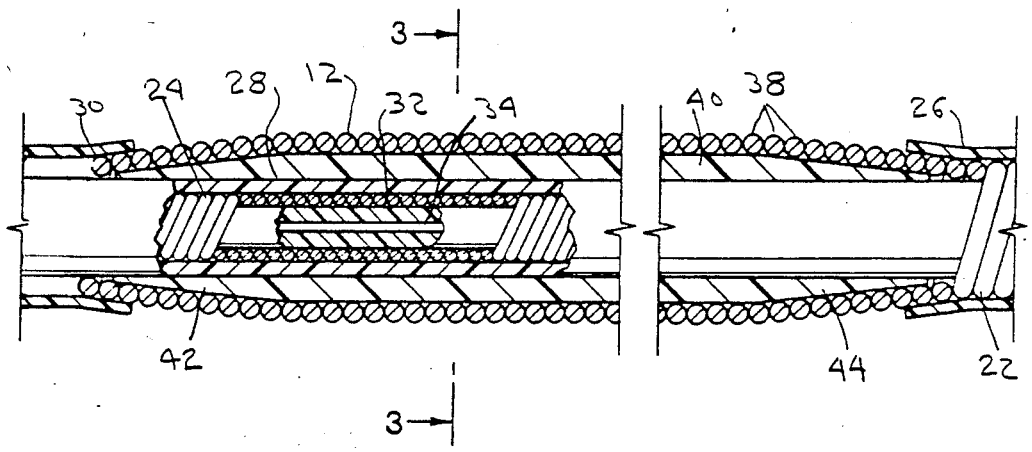
FIG. 2 is a longitudinal section through the coil electrode portion of the lead of FIG. 1.

Referring now to the drawings, a transvenous defibrillating and pacing lead 10 is an elongated flexible member having a defibrillating coil electrode 12 and a stimulating cathodic electrode 14 located at the distal end of the lead. In particular, cathodic electrode 14, which is to be employed for both pacing and sensing of the patient's heart, is located at the tip 16 of lead 10 and is electrically isolated from the coil electrode 12. The coil electrode 12 and cathodic electrode 14 are electrically coupled to respective separate connectors 18 and 20 at the proximal end of lead 10 by separate conductor coils 22 and 24. The latter coils are individually encased in separate conventional insulating sheaths 26 and 28 which are compatible with body tissue and fluids, such as polyurethane or silicone rubber, for electrical isolation of the respective conductive coils and associated electrodes.

Figure 3:
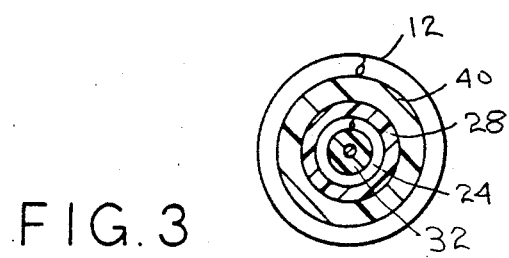
FIG. 3 is a transverse section taken along line 3—3 of FIG. 2.

Conductor coil 22 is electrically and physically a continuous extension of coil electrode 12, except that the conductor portion 22 is covered by insulating sleeve 26 whereas the entire surface area of electrode portion 12 is exposed. The coil electrode 12 terminates at a point 30 spaced back from the cathodic electrode 14. Conductor coil 24 is electrically connected to cathodic electrode 14 in a conventional manner, and is of smaller diameter throughout than conductor coil 22, such that coil 24 fits within the inner diameter of sheath 28 and coil 22 (and, of course, within the inner diameter of coil electrode 12) over their common length in lead 10, as best seen in FIG. 3. Coil 24 can be supported by an innermost insulator 32.

Cathodic electrode 14 may be composed of an electrically conductive material conventionally used for pacing electrodes, such as titanium, platinum-iridium or platinum, and may have its surface coated with a layer to be described presently. Conductor coil 24 for the cathodic electrode 14 is preferably composed of MP35N alloy (an alloy comprising nickel, cobalt, chromium and molybdenum manufactured by Maryland Specialty Wire Company of Cockeysville, Md. The composition and fabrication of the coil constituting conductor 22 and electrode 12 will be described presently.

The connector assembly includes male connector 18, electrocally connected to conductor coil 22 and defibrillating coil electrode 12, and male connector 20, electrically connected to conductor coil 24 and cathodic electrode 14. Each connector 18, 20 is adapted to mate with a female connector assembly (not shown) of a suitable implantable cardiac stimulator, such as that disclosed in co-pending U.S. patent application Ser. No. 875,218 of Haluska, et al. filed June 17, 1986, and assigned to the same assignee as the present application and the disclosure of which is incorporated therein by reference. By virtue of such connection through the male and female connector assemblies, the coil electrode 12 will be electrically connected to a defibrillator section and the cathodic electrode 14 will be electrically connected to a pulse generator and sense amplifier section of the cardiac stimulator. Alternativley, the respective electrodes may be electrically connected to conventional separate implantable pulse generator and implantable defibrillator.

Connector 20 is constructed in a conventional manner to accept a stylet 34 to enable the implanting physician to secure the lead 10 in place in the heart by means of a positive or active fixation mechanism, such as corkscrew 36 which preferably has a blunt tip to avoid becoming hung up during insertion of the lead. Fixation is implemented when the cathodic electrode 14 is properly positioned in stimulating relationship with excitable myocardial tissue in the right ventricle to achieve capture and to permit sensing ECG signals. The stylet is also useful for removing the embedded corkscrew from surrounding tissue whenever it is desired to withdraw the transvenous lead 10.

According to the invention, the defibrillating coil comprising the electrode portion 12 and the conductor portion 22 is composed of a plurality of separate wires 38 which are wound side-by-side in a multi-filar configuration on support tube 40 to form a tight coil which is relatively flexible. Each of the individual wires is composed of a copper-zirconium alloy core wrapped by an outer layer of tantalum, and is available from the Heraeus Group of West Germany. In the preferred embodiment, coil electrode 12 consists of three separate wires 38 of the aforementioned composition closely wound into a trifilar coil, and has an overall coil length in the range from six to ten centimeters. Each wire has a diameter of approximately 0.20 millimeter, and a tantalum wrap or cladding thickness of about 0.05 millimeter. As noted above, coil electrode 12 is a continuation of coil conductor 22, the overall coil being fabricated as one continuous trifilar coil of the tantalum-wrapped copper-zirconium wire composition, and thus, is relatively simple to manufacture.

The plural wires and their composition provide coil electrode 12 with certain highly desirable properties for its use in defibrillation. These include high tensile strength (1,000–1,100 N/mm$^2$), breaking weight (12.5 N), hardness (240–270 HV, Vickers), grain size (3–4.5 ASTM), and low impedance (for example, a 0.2 mm trifilar coil with coil diameter of 0.9 mm and length of 630 mm has a total resistance of about one ohm). Furthermore, the multi-filar coil readily withstands the voltage levels necessary for defibrillating shocks.

The coil electrode 12 lies outside the insulative sheath 26 and upon the profiled support tube 40. The support tube 40 is formed from insulative material and is positioned on insulated sleeve 28. The coil electrode 12 is flared from end portions 42, 44 from a minimum diameter in the range of about 0.068 to 0.079 inch, to a maximum diameter in the range from about 0.118 to 0.131 inch over the more than 90% of its length. The electrode coil 12 provides a large electrode surface area in proportion to a physical area (the chamber in which it is adapted to be positioned) of relatively small size, and thereby significantly enhances the efficient transfer of energy to tissue of the chambers of heart in fibrillation, in the delivery of the defibrillating shock.

In the preferred embodiment, the exposed outer surface of the coil electrode 12, including the tapered ends thereof, is coated with an iridium oxide layer of 100 namometers or more in thickness. This coating is applied by one of the techniques disclosed in U.S. Pat. Nos. 4,679,572 and 4,762,136 to Baker, Jr., both of which are assigned to the same assignee as the present application and the disclosures of which are incorporated herein by reference. The cathodic electrode pacing tip 14 may also be, and preferably, is coated with such an iridium oxide layer, in the same manner. The layer of iridium oxide serves to provide both electrodes with low threshold and polarization. Neither of the conductor coils 22 or 24 is coated with an iridium oxide layer since, as previously noted, each is covered with an electrically insulative sleeve.

In use, the catheter lead 10 is implanted in the patient by threading it transvenously through the superior vena cava, the right atrium and into the right ventricle, to place tip electrode 14 in stimulating and sensing relationship to excitable myocardial tissue at the apex of the ventricle. When the implanting physician determines that the tip electrode 14 is properly positioned by the sensing of capture, the stylet 34 is manipulated to embed the corkscrew 36 in the tissue and thereby affix the cathodic electrode 14 in place in the ventricle. Positioned in that manner, the coil electrode 12 constitutes a flexible large surface area electrode which readily conforms to the shape of the ventricle wall and which is thereby distributed along the entire length of the ventricle. The length of the coil electrode 12 may be such to allow it to extend not only the entire length of the right ventricle but into the right atrium as well.

For purposes of pacing of the patient's heart, cathodic electrode 14 is electrically energized by an associated pulse generator (not shown) via conductor coil 24, and the pacing may be either unipolar or bipolar, as desired, by use of appropriate anodic electrode configurations. For unipolar pacing, the anode is conventionally integral with the case that houses the pulse generator, and the electrical circuit is completed through the body tissue and fluid. To permit bipolar pacing, an anodic electrode in the form of a ring electrode (not shown), displaced slightly back from and electrically isolated from the tip electrode 14, may be provided on the lead. Alternatively, the defibrillator coil electrode 12 may be used as the anode.

For use of transvenous lead 10 in defibrillating the patient's heart, high voltage shocks are to be applied across the defibrillating coil electrode 12 and a patch electrode (not shown) electrically isolated therefrom and implanted subcutaneously in the patient's chest in proximity to the ventricles. Alternatively, the defibrillating shocks may be delivered between the coil electrode and the metal case of the pacing pulse generator. Preferably, the implanted defibrillator, to which the coil electrode 12 of the transvenous lead and the patch electrode are separately connected, is arranged and adapted to deliver a high voltage biphasic waveform of the type described in co-pending U.S. patent application Ser. No. 019,705 of Baker, Jr., et al. filed Feb. 27, 1987, and assigned to the same assignee as the present application and the disclosure of which is incorporated herein by reference. Upon detecting ventricular fibrillation, the implanted defibrillator responds by delivering such a biphasic waveform, or other selected high voltage shock, to break the disorganized random contractions of individual sections the ventricular tissue and re-establish systematic rhythmical contractions of the entire mass of tissue.

Transvenous electrodes of the type described herein have been found to be successful in defibrillating human hearts at energy levels in the 7 to 10 joule range; which is at the lower end of the defibrillation energy range experienced for implantable automatic defibrillators and patch electrodes of the prior art, and with the decided advantage that thoracic surgery is not required to place the electrode. Moreover, unlike defibrillating catheter electrodes of the type heretofore disclosed, as in the above-mentioned Heilman, et al. U.S. Pat. No. 4,662,377, the transvenous electrode of the present invention is relatively simple to manufacture and delivers substantially all of the defibrillating shock energy to the ventricular mass.

Although a preferred embodiment of the invention has been described herein, it will be apparent to those of ordinary skill in the art that variations and modifications of the disclosed embodiment may be implemented without departing from the concepts, spirit and scope of the invention. Accordingly, it is intended that the invention is to be limited only as required by the appended claims and the applicable rules of law.

What is claimed is:

1. A transvenous catheter lead for introduction into the right side of the heart of a cardiac patient for delivering defibrillating shocks to the heart, said lead being an elongated member with electrical connector means at a proximal end, electrode means at a distal end, and first conductor means interconnecting the connector means and the electrode means, the lead having an enlarged flexible portion subjacent to the electrode means for supporting the electrode means, the electrode means comprising a defibrillating electrode coil having an electrically conductive surface exposed along a portion of said lead adjacent said distal end, said coil being a continuation of the conductor means connected to the electrical connector means and being wound on the enlarged flexible portion so that its mid-section has a diameter exceeding the diameter of its ends, and means to secure at least said distal end of said lead in the ventricle of the heart whereby said electrode coil extends substantially the entire length of the right ventricle for delivering defibrillating shocks to the ventricular mass.

2. The lead according to claim 1, wherein said lead further comprises a pacing electrode means positioned at the distal end of said lead and electrically isolated from said electrode coil for use in electrically stimulating myocardial tissue and in sensing the response of the heart to the stimulation and to the delivery of the defibrillating shocks, and second conductor means connecting said pacing electrode means to second connector means at the proximal end of the lead.

3. The lead according to claim 2, wherein said pacing electrode means comprises a stimulating cathodic electrode coated with a layer of iridium oxide.

4. The lead according to claim 2, further comprising means forming a passage for a stylet to engage and position said securing means.

5. The lead according to claim 4, wherein said first and second conductor means are coaxial coils the innermost coil forming said stylet passage.

6. The lead according to claim 1, wherein the enlarged portion comprises tapered outer end portions leading to a central portion of uniform dimensions.

7. The lead according to claim 6 wherein the enlarged portion comprises a sleeve having an axial passage.

8. The lead according to claim 7 wherein the sleeve comprises an elastomeric insulating material.

9. The lead according to claim 8, wherein said electrode coil comprises a plurality of wires tightly wound in a multi-filar configuration.

10. The lead according to claim 9, wherein each of said wires is composed of copper-zirconium alloy wrapped with tantalum.

11. The lead according to claim 10, wherein the surface of said electrode coil exposed along said lead is coated with a layer of iridium oxide.

12. A transvenous defibrillating lead for use with an implantable cardiac stimulator, said lead being an elongated member with distal and proximal ends and comprising at least first and second electrical connector means at said proximal end of said lead, pacing electrode means at the distal end of said lead, first conductor means connecting said pacing electrode means to said first connector means for use in delivering pacing stimuli to excitable cardiac tissue of a chamber in the right side of the heart, and coil electrode means adjacent to and spaced from said pacing electrode means and comprising tightly wound wire forming an electrically-conductive coil wound on an enlarged flexible support means and exposed along a limited portion of the length of said lead and second conductor means connecting said coil to said second connector means for use in delivering defibrillating stimuli to tissue of a selected chamber of the heart, said exposed limited portion arranged and adapted to be disposed along substantially the entire length of said selected chamber when said pacing electrode means is properly positioned, said flexible support means being flared to provide a greater diameter along the mid-section thereof than the diameter at either end, and means to fix said distal end of said lead with respect to said heart.

13. The lead according to claim 12, wherein the flexible support means comprises tapered outer end portions leading to a central portion of uniform dimensions.

14. The lead according to claim 13 wherein the flexible support means comprises a sleeve having an axial passage.

15. The lead according to claim 14 wherein the sleeve comprises an elastomeric insulating material.

16. The invention according to claim 15, wherein said coil comprises a plurality of wires tightly wound side-by-side to form a multi-filar coil.

17. The invention according to claim 16, wherein each of said conductor means are composed of copper-zirconium alloy wrapped with tantalum.

18. The invention according to claim 17, wherein the exposed surfaces of said second conductor means is coated with a layer of iridium oxide.

19. The invention according to claim 12, wherein the exposed surface of said coil along said limited portion is coated with iridium oxide.

20. The invention according to claim 19, wherein said pacing electrode means comprises a stimulating cathodic electrode coated with a layer of iridium oxide.

21. The invention according to claim 12, wherein a distal end of said coil is spaced from said pacing electrode means by approximately one centimeter, and said coil has an exposed length in the range of from six to ten centimeters.

22. The invention according to claim 12, wherein one of said conductor means is in the form of a coil extending between said first electrical connector means and said pacing electrode means further comprising a stylet capable of passing through said conductive coil to engage and position said fixation means.

23. A defibrillating lead comprising flexible elongate electrically conductive means of predetermined length and enclosed within an insulative sheath for transvenous introduction into the heart, electrical connector means on a proximal end of said conductive means, a flexible tightly wound electrically conductive coil integral with said elongate conductive means and adjacent a distal end thereof, said coil having an exposed length sufficient to be disposed along substantially the entire length of a chamber of the heart to be defibrillated when said lead is positioned for defibrillation, a first insulative sleeve enclosing said conductive means and a second flexible insulative sleeve received on said first sleeve and supporting said coil, said second insulative sleeve being flared from a first smaller diameter at either end thereof to a second larger diameter intermediate its ends whereby a relatively large electrically conductive surface area is exposed within said chamber.

24. The lead of claim 23, wherein said conductive means and said coil are fabricated from wire composed of copper-zirconium alloy clad with tantalum.

25. The lead of claim 24, wherein said wire is coated with iridium oxide at least along the exposed length thereof.

26. The lead of claim 23, wherein said coil length is sufficient for the coil to extend as well into a adjacent chamber on the same side of the heart.

27. The lead of claim 23, further comprising fixation means to secure at least the distal end of said lead to cardiac tissue.

28. The lead according to claim 23, wherein the second insulative sleeve comprises tapered outer end portions leading to a central portion of uniform dimensions.

29. The lead of claim 28, wherein said conductive means and said coil are composed of a multi-filar winding.

* * * * *